United States Patent
Robertson et al.

(10) Patent No.: US 8,932,640 B2
(45) Date of Patent: Jan. 13, 2015

(54) PROCESS FOR PREPARING A PARTICLE COMPRISING A BIOLOGICAL MOLECULE AND A CARRIER POLYMER

(75) Inventors: John Robertson, Harlow (GB); Kenneth Baird Smith, Harlow (GB)

(73) Assignee: Glaxo Group Limited (GB)

( * ) Notice: Subject to any disclaimer, the term of this patent is extended or adjusted under 35 U.S.C. 154(b) by 672 days.

(21) Appl. No.: 12/278,855

(22) PCT Filed: Feb. 8, 2007

(86) PCT No.: PCT/EP2007/051225
§ 371 (c)(1), (2), (4) Date: Aug. 8, 2008

(87) PCT Pub. No.: WO2007/090870
PCT Pub. Date: Aug. 16, 2007

(65) Prior Publication Data
US 2009/0318539 A1 Dec. 24, 2009

(30) Foreign Application Priority Data

Feb. 9, 2006 (GB) .................................. 0602637.1

(51) Int. Cl.
*A61K 38/28* (2006.01)
*A61K 48/00* (2006.01)
*A61K 9/14* (2006.01)
*A61K 9/16* (2006.01)

(52) U.S. Cl.
CPC ................. *A61K 48/00* (2013.01); *A61K 9/146* (2013.01); *A61K 9/1647* (2013.01); *A61K 9/1682* (2013.01)
USPC ........... 424/499; 424/489; 424/491; 514/44 R (58) Field of Classification Search
CPC ..... A61K 9/146; A61K 48/00; A61K 9/1682; A61K 9/1647
See application file for complete search history.

(56) References Cited

U.S. PATENT DOCUMENTS

| 5,043,280 A | 8/1991 | Fischer et al. |
| 5,783,567 A | 7/1998 | Hedley et al. .................... 514/44 |
| 6,610,223 B2 * | 8/2003 | Lee .................................... 264/9 |
| 6,838,089 B1 * | 1/2005 | Carlsson et al. .............. 424/450 |
| 2002/0114844 A1 * | 8/2002 | Hanna et al. ................... 424/490 |
| 2004/0053873 A1 | 3/2004 | Barman et al. .................. 514/44 |
| 2005/0191491 A1 * | 9/2005 | Wang et al. ................... 428/407 |

FOREIGN PATENT DOCUMENTS

| WO | WO 91/09079 | 6/1991 |
| WO | WO 94/23738 | 10/1994 |
| WO | WO 94/23738 A | 10/1994 |
| WO | WO 98/31398 | 7/1998 |
| WO | WO 99/52507 | 10/1999 |
| WO | WO 03/070905 | 8/2003 |

OTHER PUBLICATIONS

Elvassore et al., Ind. Eng. Chem. Res. 2001, 40, 795-800.*
Yeh, et al. *Journal of Controlled Release*, 33(3): 437-445 (1995).

* cited by examiner

*Primary Examiner* — Doug Schultz
(74) *Attorney, Agent, or Firm* — Jason C. Fedon; William T. Han (57) ABSTRACT

A process for preparing a particle comprising a biological molecule typically a DNA plasmid, and a carrier polymer, typically poly-lactic acid (PLA), in which an organic solvent solution of the biological molecule and the carrier polymer in an organic solvent medium, nearly saturated with the biological molecule, is prepared, then this solution is contacted with an antisolvent substance, typically supercritical carbon dioxide to separate a particle comprising the biological molecule and the carrier polymer. High loadings of the biological molecule in the particle can be achieved.

16 Claims, 4 Drawing Sheets

Lane 1: 1Kb+ marker
Lane 2: 1μl Chloroform/TE extract
Lane 3: 2μl Chloroform/TE extract
Lane 4: 5μl Chloroform/TE extract
Lane 5: 1μg precipitated using EtOH
Lane 6: TE wash, precipitated using EtOH
Lane 7: 1μg DNA extracted with DCM/TE & precipitated using EtOH
Lane 8: 1μg DNA from filter & precipitated using EtOH
Lane 9: 100ng input DNA
Lane 10: 500ng input DNA
Lane 11: 1μg input DNA
Lane 12: 1Kb+ marker

PROCESS FOR PREPARING A PARTICLE COMPRISING A BIOLOGICAL MOLECULE AND A CARRIER POLYMER

This application is a §371 national stage entry of International Application No. PCT/EP2007/051225, filed 8 Feb. 2007, which claims priority of Great Britain Application No. GB 0602637.1, filed 9 Feb. 2006, which are incorporated herein in their entireties.

This invention relates to a process for the production of particulate carriers for delivery of bio-molecules and biologically active materials using supercritical fluid processes, to products which can be made using the process, and to an apparatus for performing this process.

Successful delivery of biologically active materials for cellular uptake following injection (IM/IV) is often limited by the ability of the body to break the active down prior to reaching the target and the ability of the target to uptake the active. For example during delivery of DNA therapies, the plasmid may be broken down by the chemicals present in the system and if the DNA is solubilised or in solution, target cells such as dendritic cells may not favour uptake of soluble material. Several strategies for overcoming this hurdle have been adopted including use of viral vectors, particulate carriers and adjuvants. Of specific interest to the present invention is the particulate carrier approach, whereby the active may be encapsulated in particulate form to afford it protection from chemical attack and to allow the particulate therapy to enter the cell by natural processes such as phagocytosis. Following entry into the cell and subsequent breakdown of the particulate carrier, the therapeutic material(s) may be released in a controlled manner and result in a therapeutic response.

To date, a variety of processing methods have been utilised as means of producing such particulate carriers with desirable physical, chemical and biological properties. One known processing method involves the use of a supercritical fluid or near critical fluid. As used herein the term "supercritical fluid" refers to a fluid substantially at or above its critical pressure (Pc) and critical temperature (Tc) simultaneously. As used herein the term "near critical fluid" refers to a fluid in which the reduced temperature (actual temperature measured in Kelvin divided by the critical temperature of the solution (or solvent) measured in Kelvin), and the reduced pressure (actual pressure divided by critical pressure of the solution (or solvent)) of the solution (or solvent) are both greater than 0.8 but the fluid is not a supercritical fluid. Correspondingly a near-critical condition for a particular fluid refers to a condition in which the reduced temperature and reduced pressure are both respectively greater than 0.8 but the condition is not supercritical. As used herein the term "fluid" can refer to both solvents and solutions in solvents. Under ambient conditions, a solvent can be a gas or liquid. The term solvent is also meant to include a mixture of two or more different individual solvents.

The use of near critical and supereritical fluids (SCF's) and the properties thereof have been extensively documented, see for example, McHugh M. A. and Krukonis V. J., Supereritical Fluid Extraction: Principles and Practice, Butterworth-Heinemann, 2nd Ed., 1994. King M. B. and Bott T. R., Extraction of Natural Products Using Near Critical Solvents, Blackie Academic and Professional, Glasgow, 1993 and Krukonis V. J., Brunner G. and Perrut M., Industrial Operations with Supercritical Fluids: Current Processes and Perspectives on the Future, Tome 1, Proceedings of the 3rd Int. Symp. on Supercritical Fluids, 1994. Supereritical fluids are of considerable interest in a number of fields of endeavour because of their unique properties. These properties include self diffusivities and viscosities approaching that of a gas, densities approaching that of a liquid and zero surface tension. Furthermore, the high compressibility of supercritical fluids implies large changes in fluid density for small changes in pressure, which in turn results in highly controllable solvation power and thus selective extraction using a single supereritical fluid is possible. Furthermore, many supercritical fluids are gases at ambient conditions of temperature and pressure, which eliminates the evaporation or concentration step needed in conventional liquid extraction. The densities of supereritical fluids typically range from 0.1-1.4 gml-1 under normal working conditions. Most of the commonly used supercritical fluids provide advantageous environments for working with compounds of low stability due to their inertness and the moderate temperatures used in routine working conditions. Carbon dioxide is the most extensively used SCF as it is cheap, readily available, inert, non-toxic, non flammable, and has a critical temperature near to ambient temperature.

There are numerous ways in which an SCF can be used. In one such class of methods the supercritical fluid is used as an anti-solvent or non-solvent. Techniques such as Gas-Anti Solvent (GAS), Supercritical Anti-Solvent (SAS), Precipitation with a Compressed fluid Anti-solvent (PCA), Aerosolised Supercritical Extraction System (ASES), and Solution Enhanced Dispersion of Solids (SEDS) are examples which fall within this class.

However in the utilisation of a supereritical fluid as an antisolvent for reformation of biological molecules such as DNA plasmids it is the case that problems are encountered in preserving the activity of the DNA or the desired structure. This has been reported in the literature by Okamoto et al. J. Pharm Sci, Vol 92, No 2, 2003 pp 371-380, Okamoto et al. Int J. Pharm, 290, (2005) pp 73-81, Tservistas et al. Biotech and Bio. Eng, Vol 72, No 1, 2001. These problems are largely encountered as a result of pH effects and proton attack as a result of using aqueous based media for dissolution of, for example DNA, molecules followed by mixing with a supercritical anti-solvent such as carbon dioxide which in the presence of water is an acid forming entity. In such cases buffers have been employed to stabilise the pH to minimise degradation of the biological molecule.

U.S. Pat. No. 5,043,280 discloses a method for the manufacture of a product having a pharmaceutical substance embedded in a carrier polymer such as polylactide, in which a liquid medium containing the substance and the carrier is fed into a supercritical gas, and separating the so-formed particles from the mixture of the medium and the gas.

U.S. Pat. No. 6,183,783 discloses a method for making microcapsules comprising an active substance coated with an encapsulating layer of a polymer film, in which the active substance is suspended in a polymer solution then the solvent is extracted away using a supercritical fluid to form the microcapsules.

U.S. Pat. No. 5,833,891 discloses a method whereby biological molecules may be embedded in polymer particles by spraying a mixed solution or suspension of the biological molecule and the polymer into a supercritical fluid.

WO-A-2004/004862 discloses a method for making particles of a substance by suspending droplets of a solution of the substance in a solvent, in an immiscible liquid then extracting away the solvent using a supercritical fluid.

WO-A-2004/006893 discloses a process for making particles which comprise a carbohydrate polymer and a biopolymer by mixing a solution containing these two with a supercritical fluid.

It is an object of this invention to provide a novel process using a supercritical fluid for formation of particles comprising a biological molecule, the term "biological molecule" as used herein including in particular a nucleic acid molecule (the term includes DNA and RNA molecules) or protein molecule, which addresses these problems of known processes.

According to this invention a process for preparing a particle comprising a biological molecule and a carrier polymer is provided, comprising the steps of:

providing a solution of the biological molecule and the carrier polymer in an organic solvent medium, in which the concentration of the biological molecule is 50% or more of the saturation concentration of the biological molecule in the solvent medium, and then contacting the solution medium with an antisolvent substance to thereby separate the biological molecule and the carrier polymer as a particle comprising both the biological molecule and the carrier polymer from the solvent medium.

Thereafter in the process of the invention the so-formed particles may be isolated and collected for use.

The process of the invention can encapsulate the biological molecule in the particles in a manner generally similar to known processes, to afford the biological molecule protection from chemical attack and to allow the particulate therapy to enter the cell by natural processes such as phagocytosis. It has surprisingly been found that using the process of this invention it is possible to employ supercritical fluid based processes, using acidic based entities such as carbon dioxide, for the production of particulate carriers for sensitive biological molecules such as DNA plasmids without quantifiable degradation, and higher loadings of biological molecules such as plasmids in the particles than achieved by alternative approaches, and advantageous therapeutic properties.

The process of the invention is preferably followed by the further step of isolating and collecting the so-formed particles. This latter step is preferably followed by the further step of formulating the so-formed particles into a medicinal formulation for use in therapy.

The term "biological molecule" herein includes peptides and peptide derivatives such as polypeptides and proteins, and nucleic acid derivatives such as DNA and RNA. The process of the invention is particularly suited to use with a biological molecule which is a DNA plasmid. It is known in the art to encapsulate such materials. The process of the invention is particularly suited to use with a biological molecule which is DNA, e.g. a DNA plasmid. DNA plasmids typically range in size from 1 to 400+ kilobase pairs (kbp). There appears to be no limitation in the size of plasmids which can be encapsulated using the present invention, and the experimental examples reported herein show encapsulation of plasmids in the range 2-10 kbp which are considered to be non-limiting and typical.

The term "carrier polymer" is a term of the art. Carrier polymers are known in the art of encapsulation of biological molecules and suitable polymers may be selected on the basis of known characteristics for biological molecules encapsulated therein. One carrier polymer or plural carrier polymers may be used. Suitable carrier polymers include polymers which are water soluble or which otherwise disintegrate in contact with water, e.g. a biodegradable polymer, so as to facilitate release of their biological molecule content following administration to a patient in need thereof. Suitable polymers include polyhydroxyacids and polymers based on polyhydroxy acids, particularly poly-(L-lactide), particularly if near critical or supercritical fluid carbon dioxide is used as the antisolvent substance. PLA is a biocompatible and biodegradable material, most commonly prepared from the cyclic diester of lactic acid by ring opening polymerization as shown below:

Lactide (Dimer of Lactic acid)

polylactide

Due to the chiral nature of lactic acid several distinct forms of PLA exist: poly-(L-lactide) being the L form typically has a crystallinity around 37%, a glass transition temperature around 50-80° C. and a melting temperature between 173-178° C.

A suitable molecular weight for such a polyhydroxy acid, particularly for PLA is in the range ca. 5000 to 150,000, preferably ca. 5,000 to 75,000. Higher molecular weights tend to result in fewer discrete particles, and slower release rates. For example the carrier polymer may comprise a mixture of two or more polymers selected from polyhydroxy acids such as a mixture of two or more polylactic acids.

The carrier polymer may incorporate other materials for example to modify its properties. For example the carrier polymer may incorporate one or more surfactant to enhance wetting of the polymer. For example the particle may include polyvinylpyrrolidone (PVP), which in the particle, e.g. in combination with PLA can modify the disintegration rate of the particle, typically by encouraging wetting of the particle. Typically the carrier polymer may contain 0.1-1.0 wt % of PVP, although a practical upper limit may be found as increasing the amount of PVP can result in a tendency to agglomeration rather than formation of discrete particles.

The weight ratio of biological molecule:carrier polymer in the solvent medium may for example be in the range 1:1000 to 1:1, preferably in the range 1:20 to 1:1. Suitable ratios to achieve a desired property of the particle may be determined experimentally. These ratios indicate a further advantage of the present invention in that particles may be made with a significantly higher loading of a biological molecule such as DNA than with prior processes.

The organic solvent medium in which the concentration of the biological molecule is 50% or more of the saturation concentration of the biological molecule in the solvent medium may comprise a single organic solvent substance or a mixture of plural solvent substances. Preferably the organic solvent medium comprises a mixture of a first organic solvent in which the biological molecule is relatively more soluble, and a second organic solvent in which the biological molecule is relatively less soluble, the carrier polymer being soluble in either or both the first and second solvents. Preferably the organic solvent medium is substantially water free, e.g. containing less than 1% v:v, preferably less than 0.5% v:v, more preferably less than 0.1% v:v water.

Preferably the process of the invention is performed by the steps of:

providing a first solution of the biological molecule in a first organic solvent, providing a second solution of the carrier polymer in a second organic solvent, mixing the first and second solutions, to thereby form a mixture of the first and second solvents in which the concentration of the biological molecule is 50% or more of the saturation concentration of the biological molecule in the so-formed mixture of first and second solvents, and then contacting the so-formed mixture with an antisolvent substance to thereby separate the biological molecule and the carrier polymer as a particle comprising both the biological molecule and the carrier polymer from the mixture of first and second solvents.

In this preferred way of performing the process the same solvent substance(s) may be used for the first solvent and second solvent. For example a first solution of the biological molecule may be prepared in a solvent at the concentration of the biological molecule of 50% or more of the saturation concentration of the biological molecule in the solvent, and a second solution of the carrier polymer may be prepared in the same solvent. The volume of second solution may be so small relative to the volume of the first solution, that when the first and second solutions are mixed the concentration of the biological molecule is 50% or more of the saturation concentration of the biological molecule in the solvent concentration of the biological molecule is still 50% or more of the saturation concentration of the biological molecule in the solvent medium so formed by mixing the first and second solutions.

Preferably in this preferred way of performing the process the first organic solvent is a solvent in which the biological molecule is relatively more soluble, and the second organic solvent is a solvent in which the biological molecule is relatively less soluble.

Suitable first organic solvents are known in which biological molecules are soluble. Preferred solvents for DNA molecules such as plasmids are polar solvents, particularly those which can co-ordinate with DNA, e.g. so-called in the art "co-ordinating solvents". Suitable first organic solvent substances for DNA molecules includes dimethyl sulphoxide (DMSO) and formamide. The first solvent may comprise a single first solvent substance or a mixture of plural solvent substances.

The first solution of a DNA molecule in the first organic solvent may be prepared by any suitable method. A suitable method comprises precipitating the DNA molecule from an aqueous solution of the DNA molecule, such molecules conventionally being stored as an aqueous solution, e.g. by adjusting the pH to a pH at which the DNA molecule precipitates out, typically as a gel, e.g. by mixing the aqueous solution with a suitable buffer such as sodium acetate (pH 5.5), and/or mixing the aqueous solution with a water-miscible organic solvent such as a $C_{1-5}$ alcohol such as ethanol. The precipitated DNA molecule may then be washed to remove contaminants such as residual salts such as sodium acetate, e.g. in an organic solvent such as a $C_{1-5}$ alcohol such as ethanol. The precipitated DNA molecule may then be maintained in contact with a water-abstracting medium, e.g. a $C_{1-5}$ alcohol such as ethanol to remove water from the precipitated DNA. The DNA may be stored in such a medium in advance of use in the process of this invention. The DNA may then be separated from the water-abstracting medium, e.g. by decanting followed by evaporation. The DNA may then be dissolved in the first solvent, e.g. DMSO.

Suitable second organic solvents are known in which known types of carrier polymer are soluble and a suitable second solvent may be chosen on the basis of the carrier polymer. The second solvent may comprise a single solvent substance or a mixture of plural solvent substances. Suitable second organic solvent substances include solvents which are less polar than the first solvent, for example substantially non-polar solvents. Suitable second solvents include halogenated hydrocarbons, e.g. $C_{1-5}$ halogenated hydrocarbon solvents, such as dichloromethane, chloroform and hexafluoroisopropanol. For example in such solvents polylactic acid is very soluble whilst DNA is practically insoluble.

The term "practically insoluble" has an accepted meaning in the pharmaceutical art e.g. as defined in pharmacopeia. Typically "practically insoluble" refers to a solubility of 1 part of biological molecule in 1,000 parts or more of second solvent, preferably 1 part of biological molecule in 5,000 parts or more of second solvent, more preferably 1 part of biological molecule in 10,000 parts or more of second solvent.

The concentration of the biological molecule is 50% or more of the saturation concentration of the biological molecule in the solvent medium, e.g. the mixture of first and second organic solvents. Preferably the concentration is 75% or more, preferably 90% or more. Most preferably the solvent medium is saturated or supersaturated with the biological molecule i.e. a solution concentration of 100% or more of the saturation concentration. This high concentration is to promote the biological molecule to come out of solution first relative to the carrier polymer, so as to be encapsulated by the carrier polymer. The saturation concentrations of biological molecules in such mixtures may be determined experimentally.

When the solvent medium comprises a mixture of first and second solvents, the above-mentioned concentration of the biological molecule may conveniently be achieved by selection of the first and second solvents and their relative ratios in the mixture. For example this may be achieved by selection of a second solvent in which the biological molecule is insoluble or practically insoluble. By mixing such a second solvent with a first solvent in which the biological molecule is soluble, a mixture of first and second solvents may be produced in which the saturation concentration of the biological molecule is less than in the first solvent. By mixing such a second solvent with a solution of the biological molecule in the first solvent the concentration of the biological molecule in the mixture relative to its saturation concentration can be increased. The concentration of the biological molecule in the mixture of first and second solvents of 50% or more of the saturation concentration encourages precipitation of the biological molecule when the mixture is contacted with the antisolvent substance.

Suitable ratios of first and second solvents in such a mixture of first and second solvents may be determined experimentally. For example in the case of a more polar first solvent such as above-mentioned DMSO or formamide, and a less polar second solvent such as above-mentioned halogenated solvents, a suitable first:second solvent volume ratio may be in the range 2:1 to 1:10, typically 2:1 to 1:5, preferably 1:1 to 1:3±10%.

When the solvent medium is achieved in the preferred method by providing a second solution of the carrier polymer in the second organic solvent and mixing this with a first solution, the concentration of the carrier polymer solution in the second solution may for example be between 0.1 to 200 mg/ml, for example between 1 to 100 mg/ml, preferably between 1 to 50 mg/ml.

First and second solutions may be mixed in various ways. In one suitable way the second solution, of the carrier polymer in the second organic solvent, may be added to the first solution of the biological molecule in the first solvent. For example the second solution may be added dropwise to the first solution, and the mixture then thoroughly mixed. However the first solution may alternatively be added to the second solution.

The solvent medium, however provided, is then contacted with an antisolvent substance to thereby separate the biological molecule and the carrier polymer as a particle comprising both the biological molecule and the carrier polymer from the medium. A preferred antisolvent substance is a supercritical fluid or near critical fluid or a liquefied gas. Preferably the pressure of the fluid is in the range 0.8-7.0 Pc, and the temperature in the range 0.8-4.0 Tc. The lower end of these pressure and temperature ranges is preferred, for convenience and to avoid any tendency to degradation of the biological molecule or carrier polymer. Suitably for the process of this invention carbon dioxide may be used as the antisolvent substance, in its supercritical state or near critical state, preferably between 25° C. to 45° C. and a pressure of 80-300 bar, typically 80-200 bar. A preferred antisolvent substance is supercritical fluid carbon dioxide. Carbon dioxide has a critical temperature of 31° C. and a critical pressure of 74 bar. Preferred processing conditions for the biological molecule DNA are 30-40° C., as above this degradation of DNA could occur. A pressure between 100-200 bar appears to be suitable as over this range there appears to be little effect on particle size. Consequently generally suitable conditions to achieve a desired particle size may be 35±5° C. and a pressure of 100±20 bar.

Other suitable materials which might be used for the antisolvent include supercritical and near supercritical nitrous oxide, carbon monoxide, ethylene. chlorotrifluoromethane, ethane, $C_1$-$C_5$ hydrofluorocarbons or derivatives thereof such as trifluoromethane, tetrafluroethane and chlorofluorocarbons.

The solvent medium, e.g. the mixture of first and second solutions may be contacted with a antisolvent substance e.g. a supercritical fluid in various ways. For example the mixing process may be a Gas-Anti Solvent (GAS), Supercritical Anti-Solvent (SAS), Precipitation with a Compressed fluid Anti-solvent (PCA), Aerosolised Supercritical Extraction System (ASES), or a Solution Enhanced Dispersion of Solids (SEDS) process.

In one way, the solvent medium is contacted with the supercritical fluid or near critical fluid, such as supercritical or near critical carbon dioxide, by containing the supercritical fluid or near critical fluid in a pressure vessel under supercritical conditions or near critical conditions, and the solvent medium is introduced under pressure into the pressure vessel. Suitably such a pressure vessel may be a flow vessel with a back pressure control on its outlet such that a suitable pressure to maintain supercritical conditions may be maintained therein whilst the material of the supercritical fluid can exit via the outlet, and thereafter decompress, and may for example carry the solvent medium out via the exit, e.g. in the vapour state.

Under such conditions the precipitation of the particles typically occurs within the pressure vessel under conditions such that the antisolvent is in a supercritical state, and the particles may be collected from the pressure vessel. Suitably collection of the particles may be achieved by de-pressurising the pressure vessel so that a supercritical fluid anti-solvent substance such as carbon dioxide converts to a gas. Suitably this de-pressurisation step may be preceded by a stage of flowing the supercritical fluid through the flow vessel to sweep residual first and second solvent from the so-formed particles.

In another way the solvent medium and the supercritical fluid may be fed along respective flow conduits to a region where the mixed solutions and the supercritical fluid meet and contact each other. A suitable apparatus for performing this last mentioned way of performing the process of the invention comprises a "T" or "Y" arrangement of tubes along two respective limbs of which first and second solutions, and the supercritical fluid may be fed, such that they may meet at the junction of the tubes and flow along and exit via the third limb. For example the solvent medium and the supercritical fluid may be fed along respective coaxial flow conduits to a region where the mixed solutions and the supercritical fluid meet and contact each other. Typically in such an arrangement the anti-solvent e.g. supercritical fluid, may be fed along the outer of two such coaxial conduits and the solvent medium along the inner.

The particles formed by the process of this invention are advantageously in the form of the biological molecule at least partly, preferably wholly, encapsulated by the carrier polymer. As mentioned above a further advantage of the present invention is that particles may be made with a significantly higher loading of a biological molecule such as DNA than with prior processes Typical prior processes achieve around 1% by weight of a biological molecule such as DNA in the particles.

Therefore in a further aspect this invention provides a particle, which may be provided by the process of this invention, comprising a biological molecule and a carrier polymer, wherein the biological molecule comprises 5% or more by weight of the particle, preferably 10% or more, more preferably 25% or more or 50% or more. Up to 99% or more of the particle may be biological molecule. In these particles the biological material may be in a state 50% or more encapsulated by the carrier polymer, preferably 90% or more encapsulated. Unencapsulated biological molecule is typically on the outer surface of the particles or unassociated with a particle. Particles having PLA as the carrier polymer typically have a size range 100 nm to 2 μm maximum dimension.

In such particles typical carrier polymers are as described above, for example polyhydroxyacids and polymers based on polyhydroxy acids as described above with respect to the process of this invention.

As described above the carrier polymer in such particles may incorporate other materials, such as polyvinylpyrrolidone (PVP) at the levels mentioned above.

Such particles may be used in therapy based on the biological molecule in the same manner as prior particles comprising a biological molecule and a carrier polymer, but the higher loading of the biological molecule achieved in the particles of this invention, e.g. the product of the process of this invention, can lead to an increased response in a patient to which they are administered. By "therapy" and derived terms herein are included both prophylactic and curative treatments.

In a further aspect of the invention there is provided a therapeutic formulation comprising the particles of the invention, provided in a form for administration to a patient in need thereof, e.g. for cellular uptake following injection (IM/IV). Such a formulation may comprise such particles made up with a suitable vehicle, e.g. with an aqueous vehicle into a form suitable for injection.

In a further aspect there is provided a method of therapeutic treatment of a human or animal in need of such treatment, comprising the step of administering to such patient such a medicinal formulation.

The invention will now be described by way of example only with reference to the following figures which show.

Figure 1:
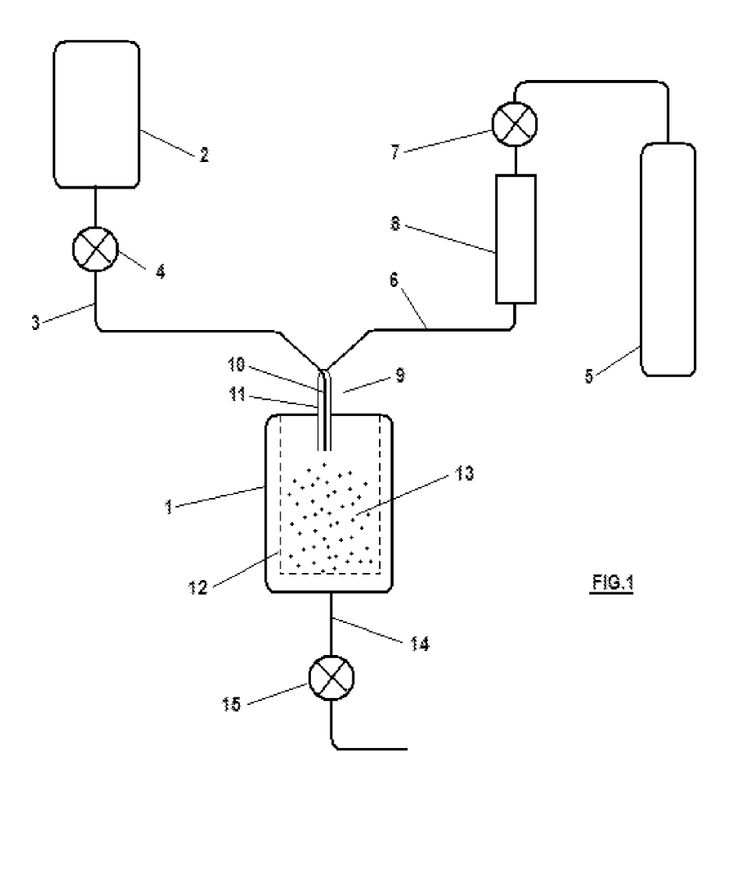
FIG. 1 is a simplified flow diagram of an apparatus as used to perform the process of this invention.

Referring to FIG. 1, a suitable apparatus for performing the process of the invention comprises a thermally controlled particle collection vessel 1 able to withstand the process temperature and pressure. A solution reservoir 2 is provided, from which a mixed solution of the biological molecule and the carrier polymer may be fed via tube 3 to pressure vessel 1 by means of pump 4. A source 5 of compressed gaseous carbon dioxide, e.g. a conventional cylinder, from which carbon dioxide may be fed via tube 6 to vessel 1, by means of pump 7. Heat exchanger 8 is provided to control the temperature of the carbon dioxide fed into the pressure vessel 1, and the pressure of the flow of carbon dioxide is also controlled so that downstream of the heat exchanger 8 the carbon dioxide is in the supercritical state. The mixed solution from reservoir 2 and the supercritical carbon dioxide are fed into vessel 1 via the coaxial nozzle 9, the solution flowing along the inner conduit 10, and the supercritical carbon dioxide flowing along the outer conduit 11. Within vessel 1 is provided filter cup 12 to catch particles 13 formed within vessel 1. The carbon dioxide and excess solvents may exit from vessel 1 via outlet tube 14, which is provided with a back pressure regulator 15 to maintain the pressure within the vessel 1 such that the carbon dioxide therein is in the supercritical or near critical state. Downstream of the regulator 15 the mixture of carbon dioxide and solvents may be fed to a suitable collection vessel (not shown) for recycling, or disposed of. The apparatus is provided with appropriate sensors and control equipment as would be understood in the art.

EXAMPLE 1

Formation of HBV-S DNA Plasmid Loaded Poly(L-Lactide) Particles

1. Preparation of a DNA Solution.

DNA plasmids were provided from an outside source. Three plasmids used were pGAG (4.9 kbp, encodes GAG antigen of HIV virus): pRNG (6.57 kbp, encodes RT, Nef and GAG antigens of HIV virus), and HBV-SAg (4.9 kbp, encodes Hepatitis B virus (HBV)). These are considered to be typical and representative DNA plasmids.

In a typical example 5 ml of lmg/ml solution of the HBV-S plasmid in PBS stored at low temperature was left to reach room temperature. To this solution 0.25 ml of sodium acetate buffer (pH 5.5) and 10 ml of absolute ethanol was added. This solution was left to stand at low temperature to allow the HBV-S plasmid to precipitate. The solution was centrifuged at 3500 rpm for 30 minutes to concentrate the plasmid. The plasmid was then washed in absolute ethanol three times to remove any remaining salts, before being stored under ethanol based media at low temperature until required.

The ethanol was poured off and the pellet left at room temperature for the bulk of the residual ethanol to evaporate off. 10 ml of analytical grade dimethyl sulfoxide (DMSO) supplied by Fischer Scientific was added. The solution was then mixed and centrifuged until all the HBV-S plasmid had gone into solution. A typical water content of the DMSO used was 0.0138% before dissolving the DNA.

An investigation was performed to see if the DNA plasmid retained its supercoiled structure after being dissolved in the organic solvents DMSO and formamide. This was done by carrying out some small scale precipitation experiments with the DNA plasmid. 100 micrograms of DNA plasmid supplied by BPD was dissolved in Iml of DMSO or formamide and the DNA solution was placed in a sealed glass pipette. The organic solvent was then stripped out by bubbling carbon dioxide through the solution using a dip tube, three precipitations being carried out with each solvent. The state of the precipitated DNA was determined by gel electrophoresis. The results from this showed that DNA can be precipitated from these solvents using carbon dioxide to strip out the solvent, and that in most of the samples at least some of the DNA's supercoiled structure was retained after precipitation. It was however found that long processing times in contact with these solvents tended to degrade the supercoiled structure of the DNA.

2. Preparation of a Polymer Solution.

50 mg of poly(l-lactide) "PLA" with an inherent viscosity of ca. 0.5 dl/g (manufacturer's specification) and a molecular weight of ca. 67,400 (manufacturer's specification) supplied by Fluka was accurately weighed out. 10 ml of analytical grade dichloromethane (DCM) was added and the solution sonicated for 10 minutes to fully dissolve the PLA.

3. Mixing of the DNA and Polymer Solutions.

The PLA/DCM solution was then added dropwise to the DNA/DMSO solution and the resulting solution mixed.

4. Contacting of the DNA and Polymer Solutions with Supercritical Fluid.

The DNA/PLA solution was then pumped into the particle collection vessel 1 through a 1/16" stainless steel tube to a 10 cm long nozzle with an i.d. of 127 μm using a Jasco PU-980 pump at a rate of Iml/min. Carbon dioxide supplied by BOC was pumped up to a pressure of 100 bar at a rate of 3 kg/hr, and was passed through a heat exchanger heating the carbon dioxide to 35° C. and into the particle collection vessel at the same time as the mixed DNA/PLA solutions where it comes into contact with the DNA/PLA solution. As the mixture of solutions contacts the supercritical carbon dioxide precipitation of the DNA and PLA as a fine powder commences.

The flow of DNA/PLA solution and carbon dioxide into the particle collection vessel was continued for 20 minutes until all the DNA/PLA solution had been pumped through. A mixture of 1:1 DCM:DMSO solution was then pumped through at 1 ml/min for 5 minutes to clear the tube of DNA/PLA solution ensuring that all the DNA/PLA solution precipitated.

The solution pump was then turned off while the flow of supercritical carbon dioxide was continued for 30 minutes. The carbon dioxide pump was then stopped and the system depressurised. Once the system had fully depressurised the sample was recovered.

The table below exemplifies a range of conditions used in fourteen experiments following the procedure of Example 1 as described above.

TABLE 1

| HBV-S Plasmid | | | | | | | | | |
|---|---|---|---|---|---|---|---|---|---|
| Expt | Plasmid Mass (mg) | PLA supplier M. Wt. | PLA Mass (mg) | Solvents (ml) DMSO | DCM | Pressure (Bar) | Temperature (° C.) | Solution Flow (ml/min) | $CO_2$ Flow (Kg/hr) |
| 1 | 0.1 | Fluka Mw ~67,000 | 10.5 | 2.5 | 7.5 | 200 | 35 | 0.1 | 1.0 |
| 2 | 0.2 | Fluka Mw ~67,000 | 4.3 | 1.0 | 3.0 | 200 | 35 | 0.1 | 1.0 |

TABLE 1-continued

HBV-S Plasmid

| Expt | Plasmid Mass (mg) | PLA supplier M. Wt. | PLA Mass (mg) | Solvents (ml) DMSO | Solvents (ml) DCM | Pressure (Bar) | Temperature (° C.) | Solution Flow (ml/min) | $CO_2$ Flow (Kg/hr) |
|---|---|---|---|---|---|---|---|---|---|
| 3 | 0.2 | Fluka Mw ~67,000 | 2.1 | 0.5 | 1.5 | 200 | 35 | 0.1 | 1.0 |
| 4 | 0.2 | Fluka Mw ~67,000 | 1.0 | 0.5 | 0.8 | 200 | 35 | 0.1 | 1.0 |
| 5 | 5.0 | Fluka Mw ~67,000 | 51.0 | 10.0 | 10.0 | 100 | 35 | 1.0 | 3.0 |
| 6 | 3.0 | Fluka Mw ~67,000 | 61.7 | 9.0 | 15.0 | 100 | 35 | 1.0 | 3.0 |
| 7 | 2.0 | Fluka Mw ~67,000 | 20.19 | 6.0 | 15.0 | 100 | 35 | 1.0 | 3.0 |
| 8 | 10.0 | Fluka Mw ~67,000 | 9.8 | 20.0 | 20.0 | 100 | 35 | 1.0 | 3.0 |
| 9 | 10.0 | Fluka Mw ~67,000 | 30.2 | 25.0 | 25.0 | 100 | 35 | 1.0 | 3.0 |
| 10 | 5.0 | Boehringer Ingelheim Mw ~5,000 | 46.0 | 15.0 | 15.0 | 100 | 35 | 1.0 | 3.0 |
| 11 | 10.0 | Boehringer Ingelheim Mw ~5,000 | 31.8 | 20.0 | 20.0 | 100 | 35 | 1.0 | 3.0 |
| 12 | 2.5 | Boehringer Ingelheim Mw ~5,000 | 47.1 | 15.0 | 15.0 | 100 | 35 | 1.0 | 3.0 |
| 13 | 5.0 | Fluka Mw ~67,000 | 48.6 | 15.0 | 15.0 | 100 | 35 | 1.0 | 3.0 |
| 14 | 2.5 | Fluka Mw ~67,000 | 48.3 | 10.0 | 10.0 | 100 | 35 | 1.0 | 3.0 |

Figure 2:
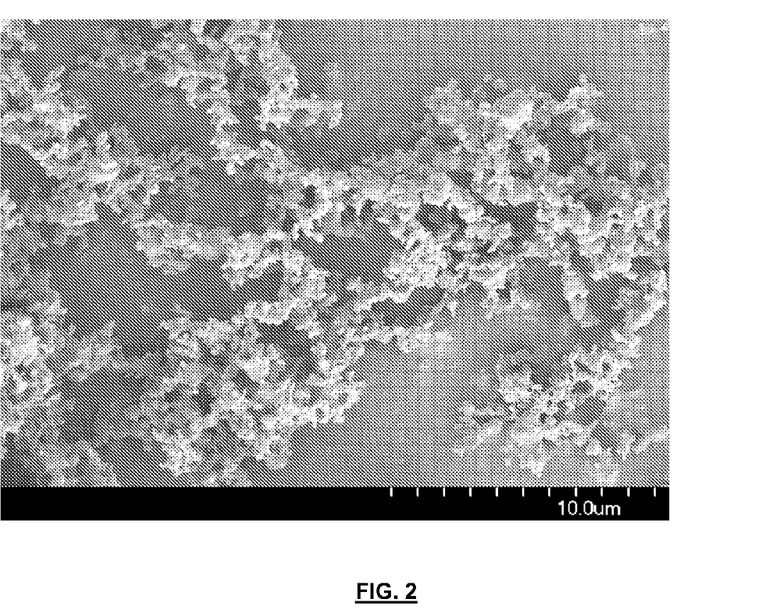
FIG. 2 is a microphotographs of particles of the invention as prepared using the process of the invention.

FIG. 2 shows a microphotographs of particles. The accompanying scale shows the size of the particles. Although samples of so-formed particles contained some tightly bound agglomerates up to around 10 microns in diameter, individual particles were formed with sizes ranging from 200 nm to 3 microns in diameter. In FIG. 2 the particles comprise 89 wt. % of a mixture of PLA of molecular weight 67,000, 10 wt % DNA plasmid and 1 wt % polyvinyl pyrrolidone.

It was found that with PLA of a molecular weight of ca. 67,000 discrete individual particles less than 2 microns diameter were formed, and any agglomerates were easily dispersed. With PLA of a molecular weight of ca. 102,000 the product was a white powder comprising discrete individual particles less than 2 microns diameter were formed, but large tightly bound agglomerates up to 200 microns were also present. With PLA of molecular weight of ca. 152,000 and 259,000 the product was a large white fluffy ball, and no individual particles were observed.

With PLA of a molecular weight of ca. 5,000 discrete individual spherical particles were formed, but were larger than particles produced using the PLA of molecular weight 67,000, and some agglomerates up to 50 microns were present. SEM showed that these particles were slightly porous, suggesting this low molecular weight PLA may be slightly soluble in supercritical carbon dioxide.

With appropriate selection of process conditions particulate sizes suitable for injection can be achieved.

Figure 6:
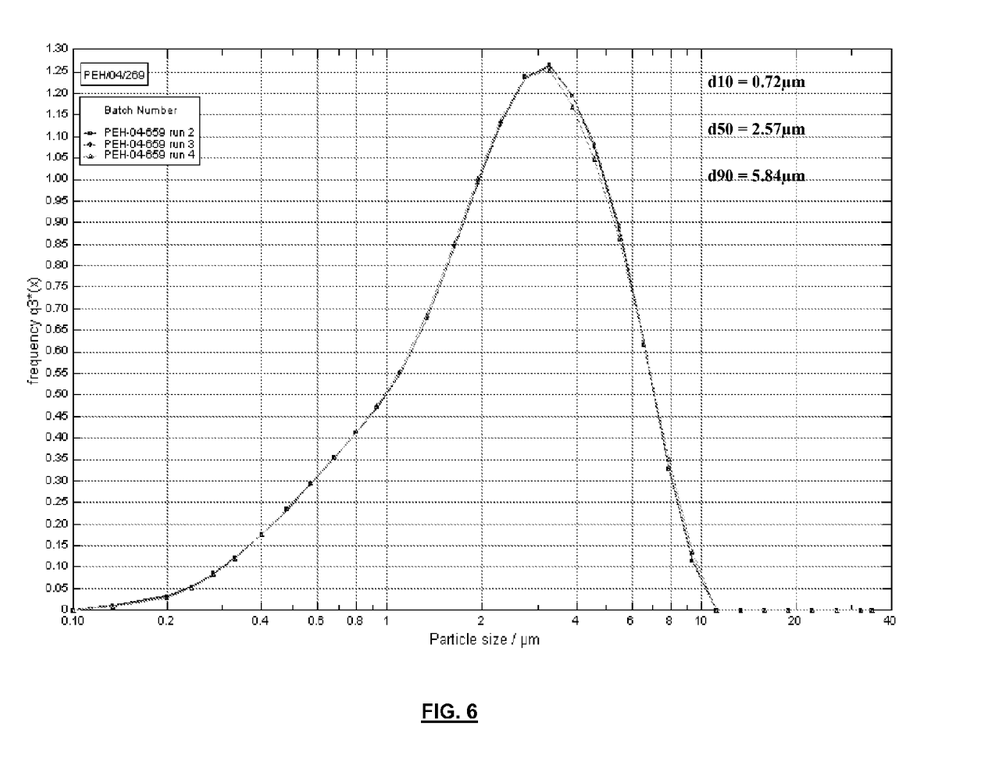
FIG. 6 shows a size distribution of particles.

FIG. 6 shows a graph of size distribution of particles formed using the above process with a PLA of molecular weight 67,000, sized on Sympatec at 0.5 bar vacuum pressure.

5. Co-Formulation with PVP.

Experiments were carried out to determine the effect of co-formulation of PVP into the carrier polymer. PVP co-formulations were prepared using the PLA of molecular weight ca. 67,000 used in the experiments above. Microscopic examination showed that the formation in number and size of agglomerates increased with increasing amounts of PVP. Samples containing up to 1 wt % PVP retained the desired particle characteristics.

To assess the wettability of the particles formed visual examinations were carried out in which 15 mg of each particle sample at varying proportions of PVP were placed in 10 ml water and shaken for 30 minutes. Results are summarized below.

| Sample | Observation |
|---|---|
| PLA + 0 PVP | Colloid formed but bulk of powder around top of vial |
| 10 wt % PVP (physical mix) | Most in colloid, still some around top of vial though less than pure PLA |
| 0.1 wt % PVP | Colloid formed but bulk of powder around top of vial |
| 0.5 wt % PVP | Colloid formed but bulk of powder around top of vial |
| 1 wt % PVP | Bulk of sample in colloid, more than 10 wt % physical mix sample. Small amount of powder around top of vial. |
| 5 wt % PVP | All powder wetted but large lumps present, 2-3 mm size |
| 10 wt % PVP | Large agglomerates floating at top of vial |
| 25 wt % PVP | All powder easily wetted but large agglomerates present |
| 50 wt % PVP | Clear liquid, big agglomerates which easily wet. |

These visual observations show that high PVP loadings improved the wettability of the PLA. Dynamic Light Scattering analysis was carried out on the samples containing the lowest amounts of PVP, samples being prepared by weighing 10 mg and adding this to 3 ml of water. The samples were then probe sonicated for 10 minutes. The count rate for each of the samples was analysed, the higher the count rate the more particles in suspension. The result showed there was a correlation between the amount of PVP and the number of particles that went into suspension:

0.1 wt % PVP Count rate=600 $kcs^{-1}$ 0.5 wt % PVP Count rate=800 $kcs^{-1}$ 1 wt % PVP Count rate=1400 kcs$^{-1}$

6. Evidence of Encapsulation of DNA in the Particles.

Figure 3:
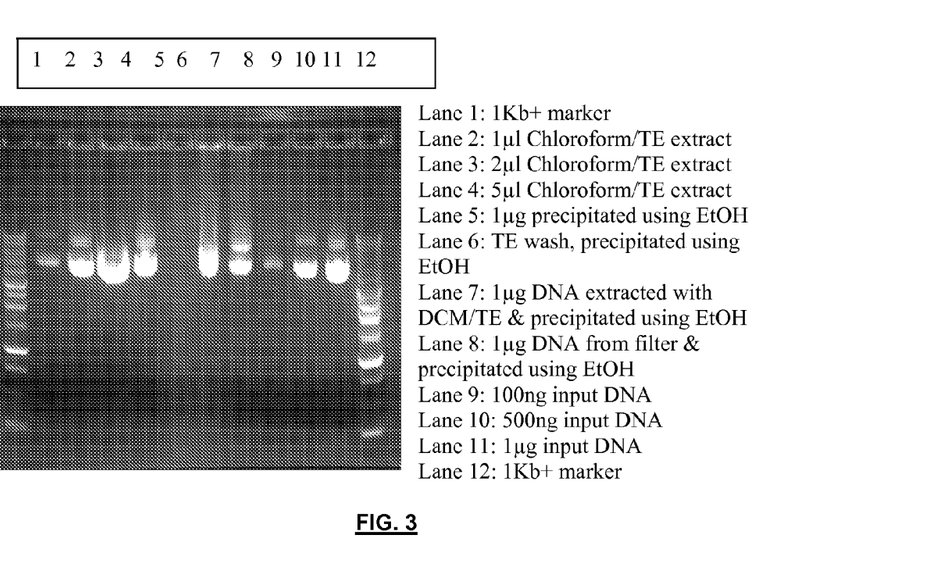
FIG. 3 is a gel electrophoresis trace showing release of DNA from particles of the invention.

FIG. 3 shows a gel electrophoresis analysis of product particles

The lanes seen in FIG. 3 are:
Lane 1: 1 Kb+ marker
Lane 2: 1 μl Chloroform/TE extract
Lane 3: 2 μl Chloroform/TE extract
Lane 4: 5 μl Chloroform/TE extract
Lane 5: 1 μg precipitated using EtOH
Lane 6: TE wash, precipitated using EtOH
Lane 7: 1 μg DNA extracted with DCM/TE & precipitated using EtOH
Lane 8: 1 μg DNA from filter & precipitated using EtOH
Lane 9: 100 ng input DNA
Lane 10: 500 ng input DNA
Lane 11: 1 μg input DNA
Lane 12: 1 Kb+ marker Lanes 1 and 12 are size markers. Lanes 2 to 4 show a 10 wt % DNA sample (67 k PLA) where the polymer has been dissolved away using chloroform then TE buffer added to extract the DNA, these lanes show that there is DNA present in the sample. Lanes 5, 7, 8, 9, 10 and 11 are various levels of the same plasmid DNA being used here as standards.

Lane 6 shows where the same sample has been washed in TE buffer to remove any loosely bound or unbound DNA. No bands are seen thus showing that the DNA is encapsulated.

The gel electrophoresis also showed that the DNA had retained the majority of its supercoiled structure.

7. Encapsulation Efficiency.

Particles with DNA loadings of 1, 5, 10, 25 and 50 wt % (the balance being carrier polymer) were prepared as described above using PLA of molecular weight ca. 67,000, and loadings of 5, 10 and 25 wt % (the balance being carrier polymer) were prepared as described above using PLA of molecular weight ca. 5,000. The encapsulation efficiency was as follows.

| Theoretical DNA Loading % | % DNA Recovery | % DNA Encapsulated | % DNA Loading |
|---|---|---|---|
| 67K PLA | | | |
| 50 | 65.6 | 75.4 | 24.9 |
| 50 | 65.6 | 72.5 | 24.0 |
| 25 | 61.7 | 88.4 | 12.9 |
| 10 | 84.3 | 97.3 | 7.3 |
| 10 | 71.3 | 98.8 | 6.6 |
| 10 | 71.3 | 98.2 | 6.5 |
| 5 | 55.5 | 92.1 | 2.5 |
| 5 | 72.2 | 99.0 | 3.5 |
| 1 | 62.8 | 97.6 | 0.6 |
| 5K PLA | | | |
| 25 | 77.0 | 98.3 | 18.1 |
| 25 | 77.0 | 98.3 | 18.1 |
| 10 | 72.8 | 77.9 | 6.5 |
| 10 | 72.8 | 78.3 | 6.6 |
| 5 | 92.1 | 88.6 | 4.1 |
| 5 | 92.1 | 89.0 | 4.1 |

8. Effect of Supercritical Carbon Dioxide on Structure of the DNA.

To determine whether supercritical carbon dioxide disrupted the supercoiled structure of DNA the process as described above was followed with pure DNA plasmid, i.e. without carrier polymer. For this purpose a 5 mg pellet of DNA plasmid was dissolved in 5 ml of DMSO and the solution subjected to the process described above. The yield from the experiment was 92% and gel electrophoresis studies showed that the DNA retained the majority of its supercoiled structure.

9. Evidence of Continued Release of Intact DNA from the Particles.

Figure 4:
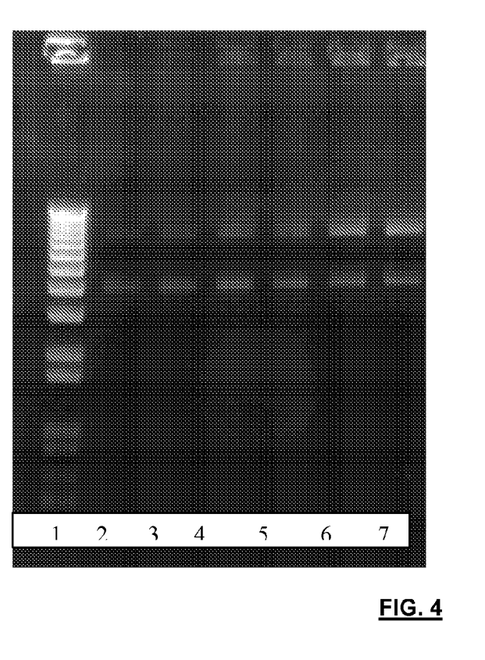
FIG. 4 is another gel electrophoresis trace showing release of DNA from particles of the invention.

FIG. 4 shows a gel electrophoresis analysis, and shows intact DNA being released from the particulate carrier over time. The release was measured by gel electrophoresis, 50 ul of a 10 mg/ml suspension of PLAs, being 10 wt % loaded samples for both 5 k and 67 k, were was used for each time point. Particles were left to incubate at RT in 50 ul TE buffer prior to running 2 ul of each sample on a 0.8% agarose gel and DNA quantification using a gene quant. Note: although not visible on this gel image release was seen from 67 k particles, however, levels of release are very low and beyond the lower detection limits of the gene quant. The important point is that the DNA is being release over time intact.

Figure 5:
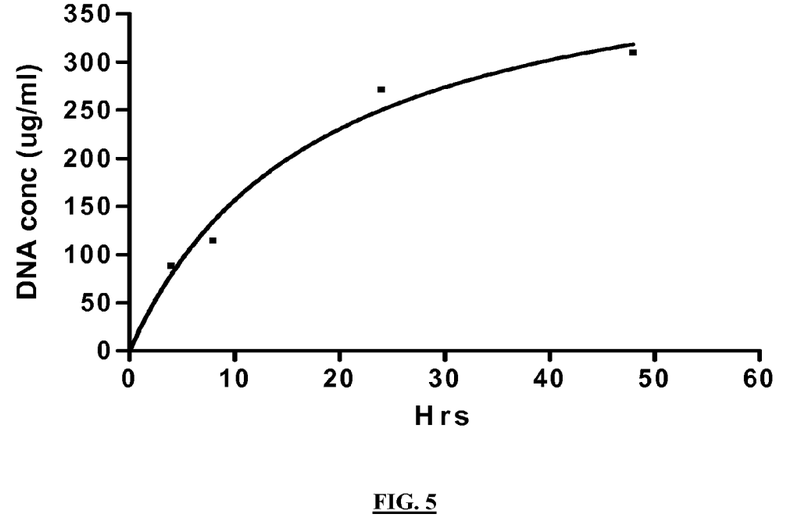
FIG. 5 shows release of DNA over time from particles of the invention.

Further evidence of continued release of DNA from the particulate carrier over time was measured by UV spectroscopy. An example release profile, taken from the gel of FIG. 3, is shown in FIG. 5 demonstrating that the DNA plasmid can be released from the carrier post injection over a sustained period of time. It was found that by modifying PLA-DNA, PLA-PLA-DNA and PLA-PVP-DNA compositions that control over the timescales and nature of release could be advantageously controlled.

10. In Vivo Study

An in-vivo study was performed in mice to assess if particles produced by the supercritical fluid process described above could produce a response in-vivo. Two formulations comprising particles formed as described above were tested alongside Gene Gun (BPDs 'Gold Std') and naked DNA plasmid.

The protocols followed for the in-vivo work were standard and according to approved methodologies.

Figure 7:
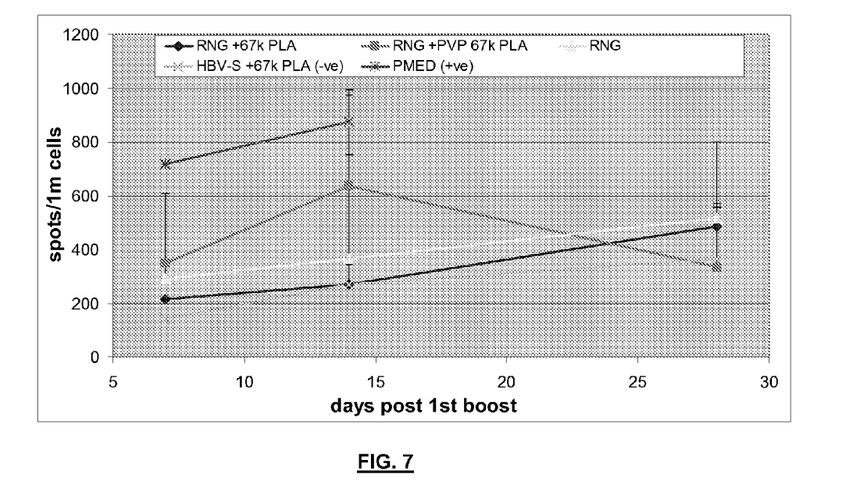
FIG. 7 shows results from an in-vivo experiment.

FIG. 7 shows the responses after 28 days. The total DNA delivered is not the same in each case. Gene Gun=1 μg, SCF=10 μg and 'naked' DNA=100 μg. A positive result was obtained. Results show that particles produced using the process of the present invention do invoke a response in-vivo giving at least 10× better response than 'naked' DNA.

The invention claimed is:

1. A process for preparing a particle comprising DNA and a carrier polymer which comprises a polyhydroxy acid or polymer based on a polyhydroxy acid having a molecular weight in the range ca. 5000 to 150,000, and wherein the carrier polymer incorporates 0.1-1.0 wt % polyvinylpyrrolidone (PVP), comprising the steps of:
  providing a solution of the DNA and the carrier polymer in an organic solvent medium being a mixture of a first, more polar, organic solvent being a $C_{1-5}$ halogenated hydrocarbon solvent in which the DNA is soluble and a second, less polar, organic solvent in which the carrier polymer is soluble and the DNA is insoluble or practically insoluble and wherein the concentration of the DNA dissolved in said medium is at least the saturation concentration of the DNA in the solvent medium, wherein the organic solvent medium contains less than 1% v:v water, and
  contacting said solution in which the concentration of the DNA dissolved in said medium is at least the saturation concentration with an antisolvent substance to thereby precipitate the DNA and separate the carrier polymer from the solution as a particle comprising both the DNA and the carrier polymer from the solvent medium.

2. The process according to claim 1, comprising a step of isolating and collecting the particle comprising both the DNA and the carrier polymer from the solvent medium.

3. The process according to claim 1, wherein the DNA is in the form of a DNA plasmid.

4. The process according to claim 1, wherein the carrier polymer comprises poly-(L-lactide).

5. The process according to claim 4, wherein the molecular weight is in the range ca. 5,000 to 75,000.

6. The process according to claim 1, wherein the carrier polymer incorporates at least one surfactant.

7. The process according to claim 1, wherein the weight ratio of DNA:carrier polymer in the solvent medium is in the range of 1:20 to 1:1.

8. The process according to claim 1 comprising: providing a first solution of the DNA in said first organic solvent, providing a second solution of the carrier polymer in said second organic solvent, mixing the first and second organic solutions, to thereby form a mixture of the first and second solvents in which the concentration of the DNA is at least the saturation concentration of the DNA in the so-formed mixture of first and second organic solvents, and contacting the mixture of the first and second organic solvents with an antisolvent substance to thereby separate the DNA and the carrier polymer as a particle comprising both the DNA and the carrier polymer from the mixture of first and second organic solvents.

9. The process according to claim 1, wherein the first organic solvent is a solvent which can co-ordinate with DNA.

10. The process according to claim 9, wherein the first organic solvent is dimethyl sulphoxide or formamide.

11. The process according to claim 1, wherein the more polar first organic solvent and the less polar second organic solvent is used in a first:second organic solvent volume ratio in the range from 2:1 to 1:10.

12. The process according to claim 1, comprising providing a second solution of the carrier polymer in the second organic solvent and mixing the second solution with a first solution of the DNA in the first organic solvent, and the concentration of the carrier polymer solution in the second solution is between 0.1 to 200 mg/ml.

13. The process according to claim 1, wherein the antisolvent substance is a supercritical fluid or near critical fluid.

14. The process according to claim 13, wherein the antisolvent substance is carbon dioxide between 25° C. to 45° C. and a pressure of 80-300 bar.

15. The process according to claim 13, wherein the solution of the DNA and the carrier polymer in the organic solvent medium and the supercritical fluid are fed along respective flow conduits to a region where the mixed solutions and the supercritical fluid meet and contact each other.

16. The process according to claim 14, wherein the antisolvent substance is carbon dioxide between 25° C. to 45° C. and a pressure of 80-200 bar.

* * * * *